(12) United States Patent
Hsu

(10) Patent No.: US 10,621,188 B2
(45) Date of Patent: Apr. 14, 2020

(54) METHODS AND ALGORITHM FOR SELECTING ALLOGENIC HEMATOPOIETIC CELL DONOR BASED ON KIR AND HLA GENOTYPES

(71) Applicant: MEMORIAL SLOAN-KETTERING CANCER CENTER, New York, NY (US)

(72) Inventor: Katharine Hsu, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 1142 days.

(21) Appl. No.: 14/776,597

(22) PCT Filed: Mar. 13, 2014

(86) PCT No.: PCT/US2014/025810
§ 371 (c)(1),
(2) Date: Sep. 14, 2015

(87) PCT Pub. No.: WO2014/151473
PCT Pub. Date: Sep. 25, 2014

(65) Prior Publication Data
US 2016/0034666 A1 Feb. 4, 2016

Related U.S. Application Data

(60) Provisional application No. 61/791,402, filed on Mar. 15, 2013.

(51) Int. Cl.
*G06F 16/248* (2019.01)
*G06F 16/2457* (2019.01)
(Continued)

(52) U.S. Cl.
CPC ...... *G06F 16/248* (2019.01); *G06F 16/24578* (2019.01); *G16B 20/00* (2019.02); *G16H 50/70* (2018.01)

(58) Field of Classification Search
CPC ........ A61K 35/12; A61K 35/28; A61K 35/30; A61K 35/51; A61K 31/7088;
(Continued)

(56) References Cited

U.S. PATENT DOCUMENTS

| | | | |
|---|---|---|---|
| 7,544,355 B2 | 6/2009 | Velardi | |
| 2011/0052554 A1 | 3/2011 | Zakrzewski et al. | |
| 2011/0129830 A1 | 6/2011 | Ladner et al. | |
| 2011/0135617 A1* | 6/2011 | Kruse ................. | C12N 5/0639 424/93.71 |
| 2011/0286467 A1 | 11/2011 | Lowther et al. | |

FOREIGN PATENT DOCUMENTS

WO 2011035870 A1 3/2011

OTHER PUBLICATIONS

Behrendt et al. "Donor killer 1-10 i1T111Jnoglobulin-like receptor genes and reactivation of cytomegalovirus after HLA-matched hematopoietic stem-cell transplantation: HLA-C allotype is an essential cofactor." Frontiers in Immunology. vol. 4, Jan. 1, 2013 (Jan. 1, 2013). XP055305276, DOI: 10.3389/finmu.2013.00036.
(Continued)

*Primary Examiner* — Joseph D Burgess
(74) *Attorney, Agent, or Firm* — Foley & Lardner LLP

(57) ABSTRACT

This disclosure is directed to a method for scoring and ranking candidate HLA-compatible unrelated hematopoietic cell donors (URD) for patients with AML or myelodysplastic syndrome. Candidate donors are scored based on KIR/HLA allele and genotype combinations. The method disclosed herein permits ranking and selection of advantageous donors that predict improved clinical outcomes of hematopoietic stem cell transplantation.

10 Claims, 1 Drawing Sheet

(51) Int. Cl.
*G16H 50/70* (2018.01)
*G16B 20/00* (2019.01)

(58) Field of Classification Search
CPC ..... A61K 49/0008; G06F 19/18; G06F 19/22; G06F 19/28; C12N 5/0639
See application file for complete search history.

(56) References Cited

OTHER PUBLICATIONS

Cooley et al. "Donors with group B KIR haplotypes improve relapse-free survival after unrelated hematopoietic cell transplantation for acute myelogenous leukemia." Blood, vol. 113, No. 3, Jan. 15, 2009 (Jan. 15, 2009), pp. 726-732, XP055305253, us ISSN: 0006-4971, DOI: 10.1182/blood-2008-07-171926.

Gagne et al. "Donor KIR3DL1/3DSI 1-10 Gene and Recipient Bw4 KIR Ligand as Prognostic Markers for Outcome in Unrelated Hematopoietic Stem Cell Transplantation." Biology of Blood and Marrow Transplantation, Kluge Carden Jennings Publishing, Charlottesville, VA, US, vol. 15, No. 11, Nov. 1, 2009 (Nov. 1, 2009), pp. 1366-1375, XP026895517, ISSN: 1083-8791, DOI: 10.1016/J.BBMT.2009.06.015 [retrieved on Oct. 12, 2009].

Supplementary European Search Report for European Patent Application No. 14769399.8 dated Oct. 7, 2016. 12 pages.

International Search Report, from the Korean Intellectual Property Office dated Aug. 19, 2014, for International Application No. PCT/US2014/025810 (filed Mar. 13, 2014), 3 pgs.

\* cited by examiner

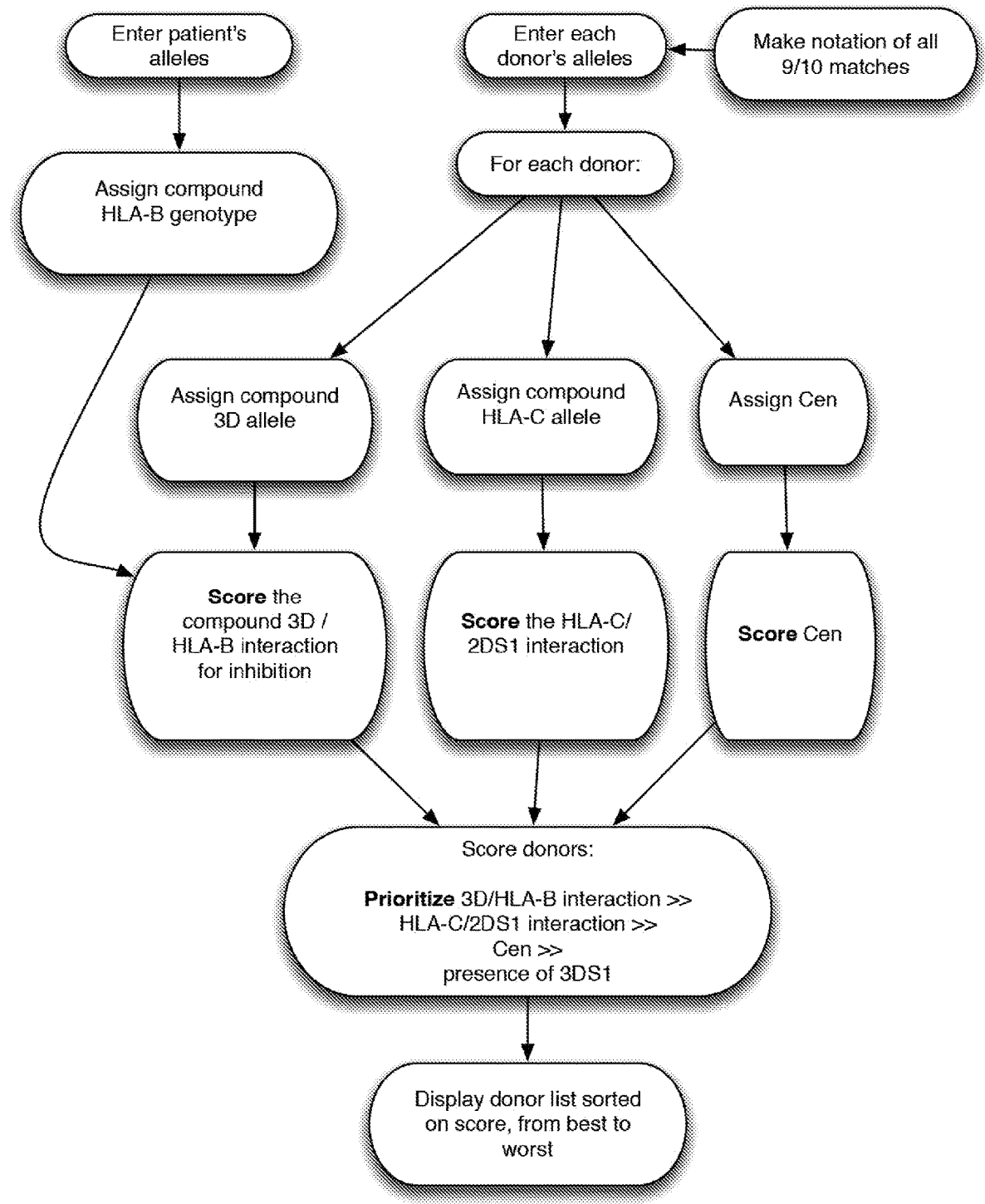

METHODS AND ALGORITHM FOR SELECTING ALLOGENIC HEMATOPOIETIC CELL DONOR BASED ON KIR AND HLA GENOTYPES

CROSS REFERENCE TO RELATED APPLICATION

This application claims the benefit of priority from U.S. Provisional Application No. 61/791,402, filed Mar. 15, 2013, the entire contents of which are incorporated herein by reference.

STATEMENT REGARDING FEDERALLY SPONSORED RESEARCH OR DEVELOPMENT

This invention was made with Government Support under Contract No. AI069197, HL088134, awarded by the National Institutes of Health. The Government has certain rights in this invention.

FIELD OF THE DISCLOSURE

This invention relates to methods and algorithm for ranking and selecting hematopoietic cell donors based on HLA and KIR genotypes.

BACKGROUND ART

Allogeneic hematopoietic stem cell transplantation (HCT) is a curative option for patients with acute myelogenous leukemia (AML), both primary AML and secondary AML evolving from a pre-existing myelodysplastic syndrome. Despite improvements in HLA genotyping where 10 allele matching is sought to improve HCT outcome, more than 50% of patients experience post-HCT complications such as relapse, CMV reactivation, and GvHD. NK cells can significantly improve risk for each of these outcomes.

Critical to innate immunity against malignantly transformed or virally infected cells, NK cells are controlled by an array of activating and inhibitory signals processed by cell surface receptors, including the KIR (Lanier, *Annu Rev Immunol* 23:225-274 (2005)). Interaction of inhibitory KIR on the NK cell surface with self-HLA class I antigens on surrounding autologous cells generates an inhibitory signal, sparing killing of autologous cells (Moesta et al., *The Journal of Immunology* 180(6):3969-3979 (2008)). In addition to the inhibitory KIR, most individuals have multiple activating KIR. Composed of up to 15 inhibitory and activating genes and pseudogenes on a single haplotype, the KIR gene repertoire is remarkably diverse with wide inter-individual genotypic variation. Reminiscent of the polymorphic diversity of the HLA region, each KIR gene has numerous alleles, with KIR3DL1 as the best characterized inhibitory KIR locus (Gardiner et al., *J Immunol* 166:2992-3001 (2001)). The clinical significance of such KIR gene diversity has focused on immune responses to viral infection (Carrington et al., *Cur Top Microbiol Immunol* 298:225-257 (2006); Martin et al., *Nat Genet* 39:733-740 (2007); Martin et al., *Nature Genetics* 31:429-434 (2002); Kamya et al., *J Virol* 85:5949-5960 (2011)) and leukemic, within the allogeneic HCT, where interactions between self and non-self occur. AML is the most common indication for allogeneic HCT, and donor NK alloreactivity can exert a potent anti-leukemic effect in this context (Ruggeri et al., *Blood* 94:333-339 (1999); Ruggeri et al., *Science* 295(5562):2097-2100 (2002)). Immunogenetics studies in HCT have evaluated the impacts of KIR/HLA compound genotypes predictive of NK alloreactivity on leukemic relapse and survival, identifying several mechanisms responsible for potent NK effects against AML (Ruggeri et al., *Blood* 94:333-339 (1999); Ruggeri et al., *Science* 295(5562):2097-2100 (2002); Ruggeri et al., *Blood* 110:433-440 (2007); Giebel et al., *Blood* 102(3):814-819 (2003); Hsu et al., *Biol Blood Mar Transpl* 12:828-836 (2006); Hsu et al., *Blood* 105:4878-4884 (2005); Cook et al., *Blood* 103:1521-1526 (2004); Stringaris et al., *Biol Blood MarrTranspl* 16:1257-1264 (2010); Venstrom et al., *Blood* 115(15):3162-3165 (2010)). NK effects against MDS are less clear, but may exist, given the pre-leukemic nature of MDS.

It is known that HLA-mismatched transplants capture NK alloreactivity through recognition on the part of donor NK cells of the lack of donor HLA KIR ligands in the recipient ("missing self" activation) (Ruggeri et al., *Blood* 94:333-339 (1999)). It has recently been shown in HLA-matched HCT, however, that strong anti-leukemic effects are associated with low-inhibitory donor KIR3DL1 allotypes and cognate HLA-Bw4 ligand allotypes (Giglio et al., *Biol Blood Marr Transpl* (2012)).

The activating KIR genes include KIR2DS1, 2DS2, 2DS3, 2DS4, 2DS5, and the 3DS1 allele of KIR3DL1. KIR2DS1-positive NK cells from HLA-C1 positive donors can mediate anti-leukemic cytotoxicity and reduce relapse post-HCT (Venstrom et al., *New England Journal of Medicine* 367:805-816 (2012)). Protective effects of the KIR2DS2-containing centromeric partial KIR haplotype (cenB) against relapse have also been reported (Cooley et al., *Blood* 113:726-732 (2009; Cooley et al., *Blood* 116:2411-2419 (2010)). Donor KIR3DS1 is also shown to be protective from GvH and transplant-related mortality (TRM) (Venstrom et al., *New England Journal of Medicine* 367:805-816 (2012); Cooley et al., *Blood* 113:726-732 (2009); Cooley et al., *Blood* 116:2411-2419 (2010); Venstrom et al., *Blood* 115:3162-3165 (2010)). Finally, donor activating KIR are protective from CMV reactivation in the patient post-HCT (Cook et al., *Blood* 107:1230-1232 (2006)).

The importance of harnessing NK alloreactivity in HCT is apparent. However, how to exploit KIR/HLA genetics for clinical benefit has been an elusive goal in allogeneic HCT, partly due to gaps in knowledge regarding the biology of KIR genes and alleles in the context of HLA.

SUMMARY OF THE DISCLOSURE

This disclosure is directed to a method for scoring and ranking candidate HLA-compatible unrelated hematopoietic cell donors (URD) for patients with AML or myelodysplastic syndrome. Candidate donors are scored based on KIR/HLA allele and genotype combinations. Specific parameters that are considered as basis of scoring include the combination of donor's compound KIR3DL1 allele type and donor/patient compound HLA-B genotype, the combination of donor's KIR2DS1 genotype and donor's compound-HLA-C genotype, donor's centromeric ("Cen") genotype assignment based on its KIR genotype, and donor's KIR3DS1 genotype. In scoring a donor, the KIR3DL/HLA-Bw combination takes priority over the KIR2DS1/HLA-C combination, which takes priority over both Cen assignment and the KIR3DS1 genotype.

This disclosure is also directed to an algorithm which can be provided on a non-transitory computer-readable medium. Such medium can be processed on a computer, for example using a CPU in the computer and causes the computer to execute the steps of the method. The computer can be a mobile device, such as a mobile telephone, PDA, or other hand-held computer, etc. In one aspect, the algorithm, or the program implementing the algorithm, can be implemented as an app on a mobile device. Further, the algorithm can be provided via cloud computing and can be accessed remotely.

The method and algorithm disclosed herein permit ranking and selection of advantageous donors that predict improved clinical outcomes of hematopoietic stem cell transplantation.

BRIEF DESCRIPTION OF THE DRAWINGS

FIG. 1 depicts a flow chart exemplifying one embodiment of this invention.

DETAILED DESCRIPTION

Disclosed herein is a method and related algorithm for ranking candidate HLA-compatible unrelated hematopoietic cell donors (URD) for patients with primary or secondary AML or myelodysplastic syndrome. Candidate donors are ranked based on KIR/HLA genotype combinations. That is, the method of this invention considers both HLA and KIR genotypes in ranking candidate donors, in contrast to the existing HLA-based donor selection scheme. Further, in ranking candidate donors, the present method prioritizes the anti-leukemic effects of inhibitory KIR/HLA combinations over the anti-leukemic effects from activating KIR.

It has been previously established that lack of HLA KIR ligands in the donor and patient is associated with some protection from leukemic relapse (Hsu et al., *Biol Blood Mar Transpl* 12:828-836 (2006); Hsu et al., *Blood* 105:4878-4884 (2005)). It has been recognized in accordance with this disclosure that inhibitory KIR/HLA combinations, particularly KIR3DL1/HLA-Bw4 combinations, are the most potent predictors of anti-leukemic NK behavior in HLA-matched HCT, superceding anti-leukemic effects from activating KIR. Less inhibitory relationships between donor KIR and recipient HLA permit higher NK activation and greater leukemic clearance.

Therefore, in accordance with a general concept underlying the method and algorithm of this invention, in order to score a candidate hematopoietic cell donor or rank a plurality of candidate donors for a patient, the relevant alleles and genotypes are determined from the patient and the candidate donor(s), and the candidate donor is then scored (and the plurality of donors are ranked) by prioritizing inhibitory KIR/HLA combinations over activating KIR/HLA combinations, which in turn take priority than two additional beneficial factors: Cen assignment based on donors' KIR genotype, and the presence or absence of KIR3DS1 in the donor(s).

By "prioritizing" or "giving priority to" a parameter, it is meant that the parameter is given more significance in the overall ranking relative to other parameters, as a result of a more significant beneficial effect of the parameter on the clinical outcome of hematopoietic cell transplantation (HCT) than other parameters. The clinical outcome of HCT is reflected by, for example, relapse, TRM (transplant-related mortality), GvHD (graft versus host disease), CMV reactivation and overall survival.

In accordance with this invention, prioritization can be achieved by assigning weight factors to various parameters, with greater weight factors given to parameters taking higher priorities. For example, four parameters can be evaluated for a patient and a candidate donor: inhibitory KIR/HLA combinations (e.g., the KIR3DL1/HLA-B combination), activating KIR/HLA combinations (e.g. the KIR2DS1/HLA-C combination), Cen (based on donor's centromeric KIR genotype), and donor's KIR3DS1 status. The ranking of priorities of these four parameters is, inhibitory KIR/HLA combinations taking priority over activating KIR/HLA combinations, which, in turn, take priority over donor's Cen and KIR3DS1 status. Each of these parameters can be scored, as further described below; and the scores are weighted with the respective weight factors assigned to the parameters, such that the weighted scores can be added together to provide a final score for the candidate donor.

Scoring a Donor Based on Inhibitory KIR/HLA Combinations

According to the present invention, the highest priority is given to inhibitory KIR/HLA combinations. In specific embodiments, for a given patient and a candidate donor, the combination of the compound KIR3DL1 allele type of the donor and the compound HLA-B genotype of either the patient or the donor is determined.

The term "compound" is used herein to reflect the combination of the maternal allele and the paternal allele for a given gene.

To determine a donor's compound KIR3DL1 (or "3DL1") allele type, both the maternal and paternal 3DL1 alleles of the donor are determined. There are four types of 3DL1 alleles: null (or "n"), low (or "l"), high ("h"), and 3DS1.

A "KIR3DL1-h", as used herein, refers to an allele which expresses the KIR3DL1 receptor at high densities on the cell surface of NK cells detectable by cell surface staining using an antibody directed to KIR3DL1 receptor (e.g., Z27 or DX9), or an allele which is yet to be characterized for surface staining but shares substantial sequence similarity to an allele which expresses the KIR3DL1 receptor at high densities on the cell surface of NK cells detectable by cell surface staining. By "substantial sequence similarity", it is meant that the relevant sequences share at least about 90%, 95%, 98%, 99% or higher identity at the nucleotide level, or at least about 90%, 95%, 98%, 99% or higher similarity or identity at the amino acid level. Documented KIR3DL1-h alleles include, for example, alleles which have been characterized by cell surface staining, including but not limited to KIR3DL1*001, *002, *008, *015, *020, *033, and *052; as well as alleles not yet characterized for surface staining but which share substantial sequence similarity to a KIR3DL1-h allele characterized by high density cell surface staining, including but are not limited to *009, *016, *043, *067, *026, *034, *035, *022, *017, *066, *029, *038, *025, *054, *018, *051, *068, *023, *028, *062, *030, *024N, *031, *042, and *057.

A "KIR3DL1-l", as used herein, refers to an allele which expresses the KIR3DL1 receptor at low densities on the cell surface of NK cells detectable by cell surface staining (e.g., using Z27 or DX9), or an allele which is yet to be characterized for surface staining but shares substantial sequence similarity to an allele which expresses the KIR3DL1 receptor at low densities on the cell surface of NK cells detectable by cell surface staining. For example, documented KIR3DL1-l alleles include alleles which have been characterized by cell surface staining, including but not limited to KIR3DL1*005, *007, and *053; as well as alleles not yet characterized for surface staining but which share substantial sequence similarity to a KIR3DL1-l allele characterized by low density cell surface staining, including but not limited to *044, and *041.

A "KIR3DL1-n", as used herein, refers to an allele which expresses KIR3DL1 molecules retained intracellularly and not detectable by cell surface staining (e.g., using Z27 or DX9), such as, e.g., *004, *019, and *056; and an allele not yet characterized for surface staining but which share substantial sequence similarity to a KIR3DL1-n allele characterized by low density cell surface staining, such as, e.g., *021, *036, *037, *039, *072, *062, and *040.

A KIR3DS1 allele expresses KIR3DS1 molecules, detectable by surface staining with Z27 but not DX9. Documented KIR3DS1 alleles include but are not limited to KIR3DS1*013, *047, *010, *011, *012, *014, *045, *046, *048, *049N, *050, *055, and *058.

To determine the 3DL1 alleles of a donor, according to one approach, the sequences of the maternal and paternal 3DL1 alleles are obtained from the donor and are compared to sequences of documented 3DL1 alleles in a database to determine whether the donor has an allele of null (or "n"), low (or "l"), high ("h"), or 3DS1. In this approach, the donor's 3DL1 allele sequences can be entered into a computer, which either hosts a database containing sequences of documented 3DL1 alleles, or has the ability to access a database not maintained on the computer which contain sequences of documented 3DL1 alleles. The computer then compares the sequences and makes a determination of the allele type based on a substantial sequence similarity between a donor sequence and a 3DL1 allele sequence in the database. Consistent with the description above, the term "substantial sequence similarity" here is meant that the relevant sequences share at least about 90%, 95%, 98%, 99% or higher identity at the nucleotide level, or at least about 90%, 95%, 98%, 99% or higher similarity or identity at the amino acid level. The computer making this comparison and determination can be the same or different from the computer which performs other steps of the present method. If different, the results of the determination of the allele types of a donor can be entered into another computer which performs other steps of the method.

In a second approach, the maternal and paternal 3DL1 alleles of the donor are determined using a non-sequencing based approach, for example, an assay based on PCR or hybridization. Determinations from such assays can be entered into and stored on a computer.

Once the maternal and paternal 3DL1 alleles of the donor are determined, a compound KIR3DL1 allele type can be assigned to the donor based on the determined maternal and paternal alleles. In certain embodiments, compound KIR3DL1 allele types are assigned according to the maternal and paternal alleles as follows:

TABLE 1

Compound 3DL allele assignment

| Genotype | Compound 3DL allele assignment |
|---|---|
| 3DL1-h/3DL1-h | 3DL1-H |
| 3DL1-l/3DL1-l | 3DL1-L |
| 3DL1-l/3DL1-h | 3DL1-L |
| 3DL1-l/3DL1-n | 3DL1-N |
| 3DL1-h/3DL1-n | 3DL1-N |
| 3DL1-n/3DL1-n | 3DL1-N |
| 3DL1-h/3DS1 | 3DL1-H |
| 3DL1-l/3DS1 | 3DL1-L |
| 3DL1-n/3DS1 | 3DL1-N |
| 3DS1/3DS1 | 3DS1 |

In addition to donor's compound KIR3DL1 allele type, the patient or donor's compound HLA-B genotype is also determined in order to determine the KIR3DL1/HLA-B combination. In most instances, a patient and a donor are matched in their HLA-B molecules, and a compound HLA-B genotype can be assigned based on either the patient HLA-B alleles or the donor alleles. In rare instances where a patient and a donor are not matched for their HLA-B molecules, the maternal and paternal HLA-B alleles are determined for the patient and for the donor, and a compound HLA-B genotype is assigned to the donor, and a different compound HLA-B genotype, if present, is assigned to the patient.

In specific embodiments, a patient and a donor are matched in their HLA-B molecules, and a compound HLA-B genotype can be assigned based on either the patient HLA-B alleles or the donor HLA-B alleles. In exemplary embodiments, the patient HLA-B alleles are determined. In one approach, the sequences of the maternal and paternal HLA-B alleles are obtained from the patient and are compared to sequences of documented HLA-B alleles in a database to determine whether the patient has an allele of HLA-Bw4 or HLA-Bw6; and if the former, whether the allele(s) is(are) Bw4-I80 or Bw4-T80, and whether the allele(s) is(are) B2705 or B57. In this approach, the patient's HLA-B sequences can be entered into a computer, which either hosts a database containing sequences of documented HLA-B alleles, or has the ability to access a database containing sequences of documented HLA-B alleles. The computer then compares the sequences and makes a determination of the types of the maternal and paternal HLA-B alleles. The computer can be the same or different from the computer which performs other steps of the present method. Other non-sequencing based approaches can also be used to determine the HLA-B genotypes, and the results of the determination can be entered and stored in a computer which performs other steps of the present method.

Once the maternal and paternal HLA-B alleles have been ascertained, a compound HLA-B genotype can be assigned. In specific embodiments, compound HLA-B genotypes are assigned based on the determined maternal and paternal HLA-B alleles as follows:

TABLE 2

Compound HLA-B genotype assignment

| Genotype | Compound HLA-B Genotype Assignment |
|---|---|
| Bw6/Bw6 | Bw6 |
| Bw6/Bw4-I80 | Bw4-I80 |
| Bw6/Bw4-T80 | Bw4-T80 |
| Bw4-I80/Bw4-T80 | Bw4-I80 |
| Bw4-I80/Bw4-I80 | Bw4-I80 |
| Bw4-T80/Bw4-T80 | Bw4-T80 |

An exception to this compound HLA-B assignment applies when an HLA-B2705 and/or HLA-B57 allele is present. B2705 and B57 are both Bw4 alleles. B57 alleles are all Bw4-I80, and most B2705 alleles are Bw4-T80. When a B2705 or B57 allele is present, the compound HLA-B genotype is assigned herein as Bw4-B2705/B57. Thus, this compound genotype includes B2705/B2705, B2705/B57, B57/B57, B2705/Bw6, B57/Bw6, and B2705 or B57 in combination with another non-B2705, non-B57 Bw4 allele.

Once the donor's compound 3DL1 allele type and the donor/patient's compound HLA-B genotype have been ascertained, the inhibitory potential between the patient and the donor can be determined as follows:

TABLE 3

Scoring based on compound HLA-B/compound 3DL combination

| Patient's or Donor's compound HLA-B | Donor's compound 3DL1 allele | Inhibition Potential | Inhibition Score |
|---|---|---|---|
| Bw4-B57/B2705 | 3DL1-H | High | Very Bad |
| Bw4-I80 | 3DL1-H | High | Bad |
| Bw4-I80 | 3DL1-L | Low | Good |
| Bw4-I80 | 3DL1-N | Null | Intermediate |
| Bw4-T80 | 3DL1-H | Low | Good |
| Bw4-T80 | 3DL1-L | High | Bad |
| Bw4-T80 | 3DL1-N | Null | Intermediate |
| Bw6 | Any | Null | Intermediate |
| Any | 3DS1 | Null | Intermediate |

HLA-B57 and B2705 alleles bind KIR3DL1-h alleles, and their interaction results in heightened NK function and inhibition. Therefore, although B2705 is not a Bw4-I80 allele, it is included with the HLA-B57 alleles as conferring a worse outcome when combined with a donor KIR3DL1-H compound allele.

For the uncommon scenario where a patient and a donor are not matched for their compound HLA-B assignment, the patient's compound HLA-B assignment will first be used in combination with the donor compound 3DL1 allele to determine the inhibition score. The donor compound HLA-B genotype may be used to determine the inhibition score if the patient is homozygous for Bw6 and the donor has a Bw4 compound assignment.

Based on the inhibitory potential, a first score is assigned to the donor, which score is inversely proportional to the inhibitory potential. In one approach, the first score can be a numeric value from 1 to 10, for example, with 1 being "very bad", 10 being "good", and other numbers in between being from bad to intermediate. For example, as shown in Table 3, with a patient's or donor's compound HLA-B of "Bw4-I80" in combination with a donor's compound 3DL1 allele of "3DL1-H", the inhibition potential is "High" which receives a first score of 2 ("bad"). Further, with a patient's or donor's compound HLA-B of "Bw4-I80" in combination with a donor's compound 3DL1 allele of "3DL1-L", the inhibition potential is "Low" which receives a first score of 10 ("good"). Still further, with a patient's or donor's compound HLA-B of "Bw4-I80" in combination with a donor's compound 3DL1 allele of "3DL1-N", the inhibition potential is "Null" which receives a first score of 5 ("intermediate"). In addition, with a patient's or donor's compound HLA-B of "Bw6" in combination with any donor's compound 3DL allele, the inhibition potential is "Null" which receives a first score of 5. Any compound HLA-B genotype in combination with a donor's compound 3DL1 allele of "3DS1", the inhibition potential is also "Null" which receives a first score of 5. Other ranges of numeric values can be used if appropriate, e.g., 1 to 20, 1 to 30, 1 to 40, 1 to 50, 1 to 60, 1 to 70, 1 to 80, 1 to 90, 1 to 100, and the like. The determination can be performed on a computer which can execute a computer program stored on non-transitory computer readable medium.

Scoring Donors Based on Activating KIR/HLA Combinations

According to the present invention, the second priority is given to activating KIR/HLA combinations. In specific embodiments, for a given patient and a candidate donor, the donor's KIR2DS1 genotype and the donor's compound HLA-C genotype are determined. The KIR2DS1/HLA-C combination is then evaluated and forms the basis for assigning a second score to the donor.

To determine a donor's compound HLA-C genotype, the sequences of the maternal and paternal HLA-C alleles are obtained from the donor and are compared to sequences of documented HLA-C alleles in a database to determine whether the patient has an allele of KIR ligand groups HLA-C1 or HLA-C2. The donor's HLA-C sequences can be entered into a computer, which either hosts a database containing sequences of documented HLA-C alleles, or has the ability to access a database containing sequences of documented HLA-C alleles. The computer then compares the sequences and makes a determination of the maternal and paternal HLA-C alleles as HLA-C1 or HLA-C2. The computer making the HLA-C allele determination can be the same or different from the computer which performs other steps of the present method. Other non-sequencing based approaches can also be used to determine the HLA-C genotypes, and the results of the determination can be entered into a computer which performs other steps of the present method.

Once the maternal and paternal HLA-C alleles have been ascertained for a donor, a compound HLA-C genotype can be assigned to the donor as follows, C1/C1, C1/C2, or C2/C2.

In addition, the status of the KIR2DS1 gene in the donor is determined. Whether the donor possesses the gene for KIR2DS1 (i.e., KIR2DS1+) or not (i.e., KIR2DS1-) can be determined by standard gene typing methods such as PCR-SSP, PCR-SSOP, or sequence-based typing.

Given the donor's KIR2DS1 genotype and the donor's compound HLA-C genotype, the donor is evaluated based on the KIR2DS1/HLA-C combination and scored as follows:

TABLE 4

Scoring a given donor's KIR2DS1 & compound HLA-C genotype

| Donor's KIR 2DS1 | Given donor's compound HLA-C genotype | Score |
|---|---|---|
| 2DS1+ | C1/C1 | Good |
| 2DS1+ | C1/C2 | Good |
| 2DS1+ | C2/C2 | Intermediate |
| 2DS1- | C1/C1 | Intermediate |
| 2DS1- | C1/C2 | Intermediate |
| 2DS1- | C2/C2 | Intermediate |

A second score is given based on the KIR2DS1/HLA-C combination. In one approach, the second score can be a numeric value from 1 to 10, with 1 being "bad", 5 being "intermediate", and 10 being "good". For example, as shown in Table 4, a donor's KIR2DS1 of "2DS1+" combined with the donor's compound HLA-C genotype of "C1/C1" determines a second score of 10 ("good"). Similarly, a donor's KIR2DS1 of "2DS1+" combined with the donor's compound HLA-C genotype of "C1/C2" determines a second score of 10. Also, a donor's KIR2DS1 of "2DS1+" combined with the donor's compound HLA-C genotype of "C2/C2" determines a second score of 5 ("intermediate"). Further, a donor's KIR2DS1 of "2DS1-" combined with the donor's compound HLA-C genotype of any of "C1/C1", "C1/C2" or "C2/C2" determines a second score of 5. Other numeric values can be used to reflect the distinctions and grades of good, intermediate and bad, e.g., 1 to 20, 1 to 30, 1 to 40, 1 to 50, 1 to 60, 1 to 70, 1 to 80, 1 to 90, 1 to 100, and the like. The determination can be performed on a computer which can execute a computer program stored on non-transitory computer readable medium.

Scoring Donors Based on Cen

A donor can be scored based on its centromeric KIR haplotype (or "Cen assignment"). Centromeric partial KIR haplotype B (or cenB) has been shown to be protective against relapse.

A donor's KIR genotype, specifically the positivity or negativity of KIR2DL1, 2DL2, 2DL3 and 2DS1, can be determined by standard gene typing methods such as PCR-SSP, PCR-SSOP, or sequence-based typing. Based on the donor's KIR genotype, a Cen assignment is determined (e.g., by a computer) for the donor according to the following:

TABLE 5

Cen assignment

| Donor KIR genotypes | Cen assignment |
|---|---|
| KIR2DL1+ and KIR2DL3+ and KIR2DL2− and KIR2DS2− | AA |
| KIR2DL1+ and KIR2DL3+ and (KIR2DL2+ or KIR2DS2+) | AB |
| (KIR2DL2+ or KIR2DS2+) and KIR2DL3− | BB |

The donor is then scored according to the Cen assignment based on the following:

TABLE 6

Scoring Cen

| Cen | Score |
|---|---|
| BB | Good |
| AA | Intermediate |
| AB | Bad |

A third score is given according to the Cen assignment. In one approach, this third score can be a numeric value from 1 to 10. For example, as shown in Table 6, when Cen is "BB", the third score is 10 ("good"). When Cen is "AA", the third score is 5 ("intermediate") and when Cen is "AB", the third score is 1 ("bad"). Similarly, other numeric values can be used if appropriate, e.g., 1 to 20, 1 to 30, 1 to 40, 1 to 50, 1 to 60, 1 to 70, 1 to 80, 1 to 90, 1 to 100, and the like, to reflect the grades from bad to good.

Scoring Donors Based on KIR3DS1

A donor can also be scored for the positivity of KIR3DS1, which has been shown to be protective from GvH and transplant-related mortality (TRM). Whether a donor is positive for KIR3DS1 or not can be determined by standard gene typing methods such as PCR-SSP, PCR-SSOP, or sequence-based typing.

A donor positive for KIR3DS1 is given a higher score to a donor negative for KIR3DS1. In one approach, this fourth score can be a numeric value from 1 to 10, with 1 as "bad" and 10 as "good". Other numeric values can be used if appropriate, e.g., 1 to 20, 1 to 30, 1 to 40, 1 to 50, 1 to 60, 1 to 70, 1 to 80, 1 to 90, 1 to 100, and the like, to reflect the grades from bad to good.

Weight Factors

In accordance with this invention, weight factors are utilized to reflect the hierarchy of priority among the parameters considered, with greater weight factors given to parameters taking higher priorities.

As described above, four parameters can be evaluated for a patient and a candidate donor: the KIR3DL1/HLA-B combination, the KIR2DS1/HLA-C combination, Cen, and KIR3DS1, and a donor is scored for each of the four parameters to provide a first, second, third and fourth scores, respectively. According to this disclosure, the KIR3DL1/HLA-B combination takes priority over the KIR2DS1/HLA-C combination, which, in turn, takes priority over Cen and KIR3DS1. A weight factor is assigned to each of the four parameters, with the weight factor assigned to the KIR3DL1/HLA-B combination being the greatest ("a first weight factor"), the weight factor assigned to the KIR2DS1/HLA-C combination being the second greatest ("a second weight factor"), followed by a third weight factor for Cen, and a fourth weight factor for KIR3DS1. In some embodiments, Cen takes priority over KIR3DS1, in which case, the third weight factor is greater than the fourth weight factor.

The scores for the four parameters are weighted with the respective weight factors, such that the weighted scores can be added together to provide a final score for a candidate donor.

In one approach, the first weight factor can be 1,000,000 (one million), the second weight factor can be 100,000 (one hundred thousand), the third weight factor can be 10,000 (ten thousand) and the fourth weight factor can be 100 (one hundred). The weight factors can be modified, as needed, to indicate the relevance of the first through fourth scores, as appropriate. For example, in one embodiment, Cen takes priority over KIR3DS1 so that the fourth weight factor can be 10,000 and the third weight factor can be 100. In other embodiments, the weight factors can be closer, such as a first weight factor of 100,000, a second weight factor of 10,000, a third weight factor of 1,000 and a fourth weight factor of 100. In still other embodiments, the weight factors can be even closer, for example, 1,000, 500, 100, and 10, respectively.

In circumstances where only one HLA-compatible candidate donor is identified for a patient, such donor is evaluated and scored according to the method disclosed herein. The score provides treating physicians and the patient a relative prospect and risks of HCT. In instances where multiple HLA-compatible donors are identified, the donors can be ranked based on scores determined according to the method disclosed herein.

Genotype frequencies among the general population and the HCT patient population (17, 18, 21, 23) support the feasibility of applying a donor selection algorithm based on KIR/HLA genotypes. HLA-Bw4 among patients occurs with frequency of 59.2%. For patients with Bw4-T80, a KIR3DL1-positive donor with a low-affinity KIR3DL1 allotype (group KIR3DL1-L) can be identified among 3 potential donors with 81% likelihood, and avoidance of a high-affinity KIR3DL1 allotype donor can occur with 98% likelihood. Likewise, for patients with Bw4-T80, identification of a KIR3DL1-positive donor with a low-affinity KIR3DL1 allotype (group KIR3DL1-H) among 3 potential donors will occur with 61% likelihood, and avoidance of a high-affinity KIR3DL1 allotype donor can occur with 92% likelihood. Frequencies of specific advantageous activating KIR genotypes occur as follows: for patients whose donors have the HLA-C1 ligand, KIR2DS1 occurs with 35% frequency; CenBB donors occur with 12% frequency, and KIR3DS1+ donors occur with 35% frequency. Among these activating KIR combinations, the likelihood of identifying one donor with at least one of these genotypes is 72%. Overall, the likelihood of identifying an advantageous donor among 3 donor choices based on KIR-HLA combinations is 70%. For HLA-Bw4 patients, the likelihood of avoiding a high-risk donor is 95% and of identifying a highly advantageous donor is 71%.

These estimations are calculated based on known KIR and HLA genotype and allotype frequencies. Therefore it is anticipated that the application of the KIR/HLA-based donor scoring and ranking algorithm disclosed herein is feasible for donor selection and will lead to improvement in post-HCT outcomes and reduction of the risks in relapse, TRM, GvHD, CMV reactivation and overall survival.

In an aspect of the disclosure, a computer includes a processor, at least one data storage device, such as, but not limited to, RAM, ROM and persistent storage, and an external interface. The processor is configured to execute one or more programs stored in a computer readable storage device. The computer readable storage device can be RAM, persistent storage or removable storage. For example, the Processor can execute instructions in a program that may be loaded into RAM. The Processor may include one or more processing units. The processor can be, but is not limited to, a CPU or a GPU.

A storage device is any piece of hardware that is capable of storing information, such as, for example without limitation, data, programs, instructions, program code, and/or other suitable information, either on a temporary basis and/or a permanent basis.

In another aspect of the disclosure, an ASIC, FPGA, a PAL and PLA can be used as the processor.

Various aspects of the present disclosure may be embodied as a program, software, or computer instructions embodied or stored in a computer or machine usable or readable medium, or a group of media which causes the computer or machine to perform the steps of the method when executed on the computer, processor, and/or machine. A program storage device readable by a machine, e.g., a computer readable medium, tangibly embodying a program of instructions executable by the machine to perform various functionalities and methods described in the present disclosure is also provided, e.g., a computer program product.

The non-transitory computer readable medium could be a computer readable storage device. A computer readable storage device, may be, for example, a magnetic, optical, electronic, electromagnetic, infrared, or semiconductor system, apparatus, or device, or any suitable combination of the foregoing; however, the computer readable storage device is not limited to these examples except a computer readable storage device excludes computer readable signal medium. Additional examples of the computer readable storage device can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an optical storage device, or any appropriate combination of the foregoing; however, the computer readable storage device is also not limited to these examples. Any tangible medium that can contain, or store, a program for use by or in connection with an instruction execution system, apparatus, or device could be a non-transitory computer readable storage device.

What is claimed is:

1. A non-transitory computer readable storage medium having computer readable program for operating on a computer for performing a method of selecting an allogeneic hematopoietic cell donor for a patient from one or more donors, said program comprising instructions that cause the computer to perform the steps of:

determining a first score for each donor of the one or more donors in accordance with the inhibition potential between the donor's assigned compound KIR3DL1 allele and the patient's and/or donor's assigned compound HLA-B genotype;

determining a second score for the donor in accordance with the KIR2DS1 genotype of the donor and the compound HLA-C genotype of the donor;

determining a third score for the donor based on a Cen assignment;

determining a fourth score for the donor based on the donor's KIR3DS1 genotype;

weighing the first, second, third, and fourth scores for each donor of the one or more donors with a first, second, third, and fourth weight factor, respectively, wherein the first weight factor is greater than the second, third, and fourth weight factors;

adding together the weighted first, second, third and fourth scores for each donor to determine a final score for each donor;

sorting the final scores of the one or more donors from highest to lowest scores to create a sorted donor list; and displaying the sorted donor list to select a subset of the one or more donors for donating allogeneic hematopoietic cell to the patient.

2. The non-transitory computer readable storage medium of claim 1, wherein the inhibition potential is determined based on the donor's assigned compound KIR3DL allele and the patient's assigned compound HLA-B genotype.

3. The non-transitory computer readable storage medium of claim 2, wherein the patient's compound HLA-B genotype is assigned by a process comprising:

determining for the maternal and paternal alleles whether the allele is Bw6 or Bw4, and if the allele is Bw4, whether it is Bw4-180, Bw4-T80, B27 or B57; and assigning the compound HLA-B genotype to the patient based on the determined maternal and the paternal alleles of the patient, wherein the compound HLA-B genotype is selected from the group consisting of Bw6, Bw4-180, Bw4-T80, and Bw4-B27/B57.

4. The non-transitory computer readable storage medium of claim 3, wherein the patient HLA-B maternal and paternal alleles are determined by comparing the patient's maternal and paternal HLA-B sequences to sequences in a database.

5. The non-transitory computer readable storage medium of claim 1, wherein the donor's compound KIR3DL1 allele type is assigned by a process comprising:

determining each of the maternal and paternal KIR3DL1 alleles of the donor as KIR3DLI-h, KIR3DL1-1, KIR3DLI-n or KIR3DS1; and assigning the compound KIR3DL allele type to the donor based on the maternal and paternal KIR3DL alleles of the donor wherein the compound KIR3DL allele type is selected from the group consisting of KIR3DL1-H, KIR3DL1-L, KIR3DL1-N and KIR3DS1.

6. The non-transitory computer readable storage medium of claim 5, wherein the donor's KIR3DLI maternal and paternal alleles are determined by obtaining the sequences of the donor's maternal and paternal alleles, and comparing the sequences to the sequences in a database comprising KIR3DL1 allele sequences.

7. The non-transitory computer readable storage medium of claim 1, wherein the second weigh factor is greater than the third weight factor, and the third weight factor is greater than the fourth weight factor.

8. The non-transitory computer readable storage medium of claim 1, wherein the computer is a mobile device.

9. The non-transitory computer readable storage medium of claim 1, wherein the computer is cloud computing and the program is accessed remotely.

10. The non-transitory computer readable storage medium of claim 1, wherein the program is implemented as an app on a mobile device.

\* \* \* \* \*